US00PP36522P2

(12) United States Plant Patent
Heinrich

(10) Patent No.: US PP36,522 P2
(45) Date of Patent: Mar. 4, 2025

(54) ***ULMUS* PLANT NAMED 'Everalan'**

(50) Latin Name: *Ulmus crassifolia*
Varietal Denomination: Everalan

(71) Applicant: Alan Heinrich, Grand Saline, TX (US)

(72) Inventor: Alan Heinrich, Grand Saline, TX (US)

(73) Assignee: TREE SAP FARMS LLC, Houston, TX (US)

( * ) Notice: Subject to any disclaimer, the term of this patent is extended or adjusted under 35 U.S.C. 154(b) by 0 days.

(21) Appl. No.: 18/799,353

(22) Filed: Aug. 9, 2024

(51) Int. Cl.
*A01H 5/00* (2018.01)
*A01H 6/00* (2018.01)

(52) U.S. Cl.
USPC ..... Plt./221

(58) Field of Classification Search
USPC ..... Plt./216, 221
See application file for complete search history.

*Primary Examiner* — Susan McCormick Ewoldt
(74) *Attorney, Agent, or Firm* — Penny J. Aguirre

(57) ABSTRACT

A new cultivar of *Ulmus* tree named 'Everalan' that is characterized by its straight central leader, its narrow, upright, and uniform plant habit, its branches that are held in 45° angles that reduces the need for pruning, its good commercial propagation from unrooted cuttings, its deciduous habit, producing few leaves persisting into late winter, its foliating bark that tends to curl in strips and reveals colorful patches of orange-tan, grey and white, its low quantity of winged branches, and its resistance to Dutch elm disease, elm leaf beetle damage, drought, wind, extreme winter and summer temperatures, and leaf scorch.

3 Drawing Sheets

Botanical classification: *Ulmus crassifolia.*
Variety denomination: 'Everalan'.

BACKGROUND OF THE INVENTION

The present invention relates to a new and distinct cultivar of *Ulmus crassifolia* and will be referred to hereafter by its cultivar name, 'Everalan'. 'Everalan' is a new cultivar of cedar elm, a deciduous tree grown for use as a landscape plant.

The new *Ulmus* was discovered as a chance seedling in a growing field of unnamed plants of *Ulmus crassifolia* in Mill Creek, Texas in December of 2018.

Asexual propagation of the new cultivar was first accomplished by stem cuttings in 2019 under the direction of the Inventor in Glen Flora, Texas. Asexual propagation by stem cuttings determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Everalan' as a unique cultivar of *Ulmus.*

1. 'Everalan' exhibits a straight central leader.
2. 'Everalan' exhibits a narrow, upright, and uniform plant habit.
3. 'Everalan' exhibits branches that are held in 45° angles that reduces the need for pruning.
4. 'Everalan' exhibits good commercial propagation from unrooted cuttings.
5. 'Everalan' exhibits a deciduous habit, producing few leaves persisting into late winter.

6. 'Everalan' exhibits exfoliating bark that tends to curl in strips and reveals colorful patches of orange-tan, grey and white.
7. 'Everalan' exhibits a low quantity of winged branches.
8. 'Everalan' exhibits resistance to Dutch elm disease, elm leaf beetle damage, drought, wind, extreme winter and summer temperatures, and leaf scorch.

Typical plants of the parent species differ from 'Everalan' in having difficulty rooting commercially, a wavy central leader, un-uniform branches that occasionally become dense on the tree interior, young branches that are typically winged, and low resistance to diseases, drought, leaf scorch and extreme temperatures. 'Everalan' can be most closely compared to the *Ulmus parvifolia* cultivars 'BSNUPF' (U.S. Plant Pat. No. 17,655) and 'Emer II' (U.S. Plant Pat. No. 7,552). 'BSNUPF' and 'Emer II' are both similar to 'Everalan' in having a large, upright plant habit. 'BSNUPF' differs from 'Everalan' in having a plant habit that broadens and does not retain a tight columnar plant habit, branch tips that splay outwards and leaves that are larger in size. 'Emer II' differs from 'Everalan' in having a vase-shaped habit with arching branches.

BRIEF DESCRIPTION OF THE DRAWINGS

The accompanying color photographs illustrates the overall appearance and distinct characteristics of the new *Ulmus*. The photographs were taken of a 4-year-old tree of 'Everalan' as grown outdoors in a landscape in Glen Flora, Texas.

The photograph in FIG. 1 provides a side view of a plant of 'Everalan' in summer.

Figure 1:
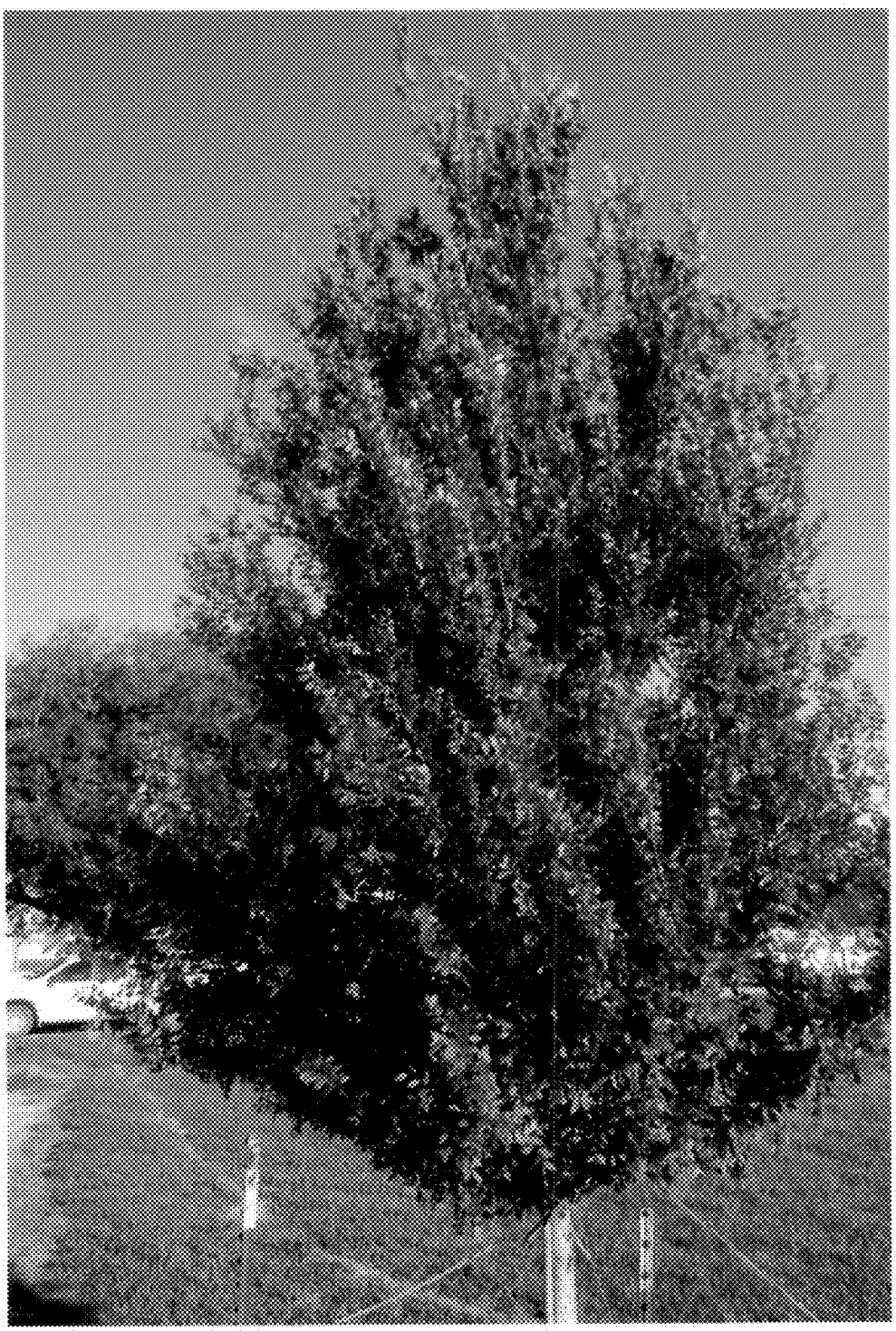
Figure 2:
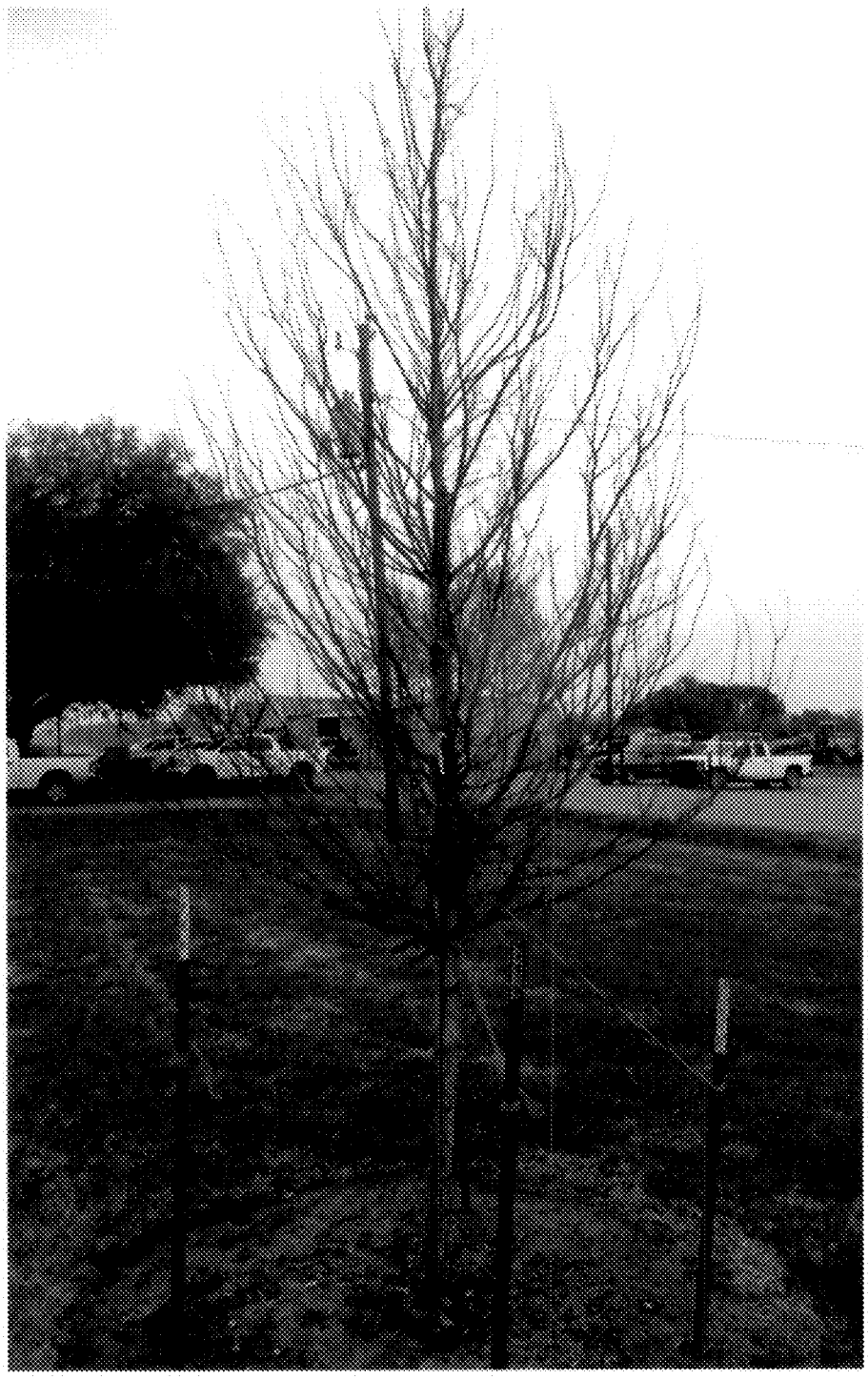

The photograph in FIG. 2 provides a view of a dormant tree of 'Everalan'.

Figure 3:
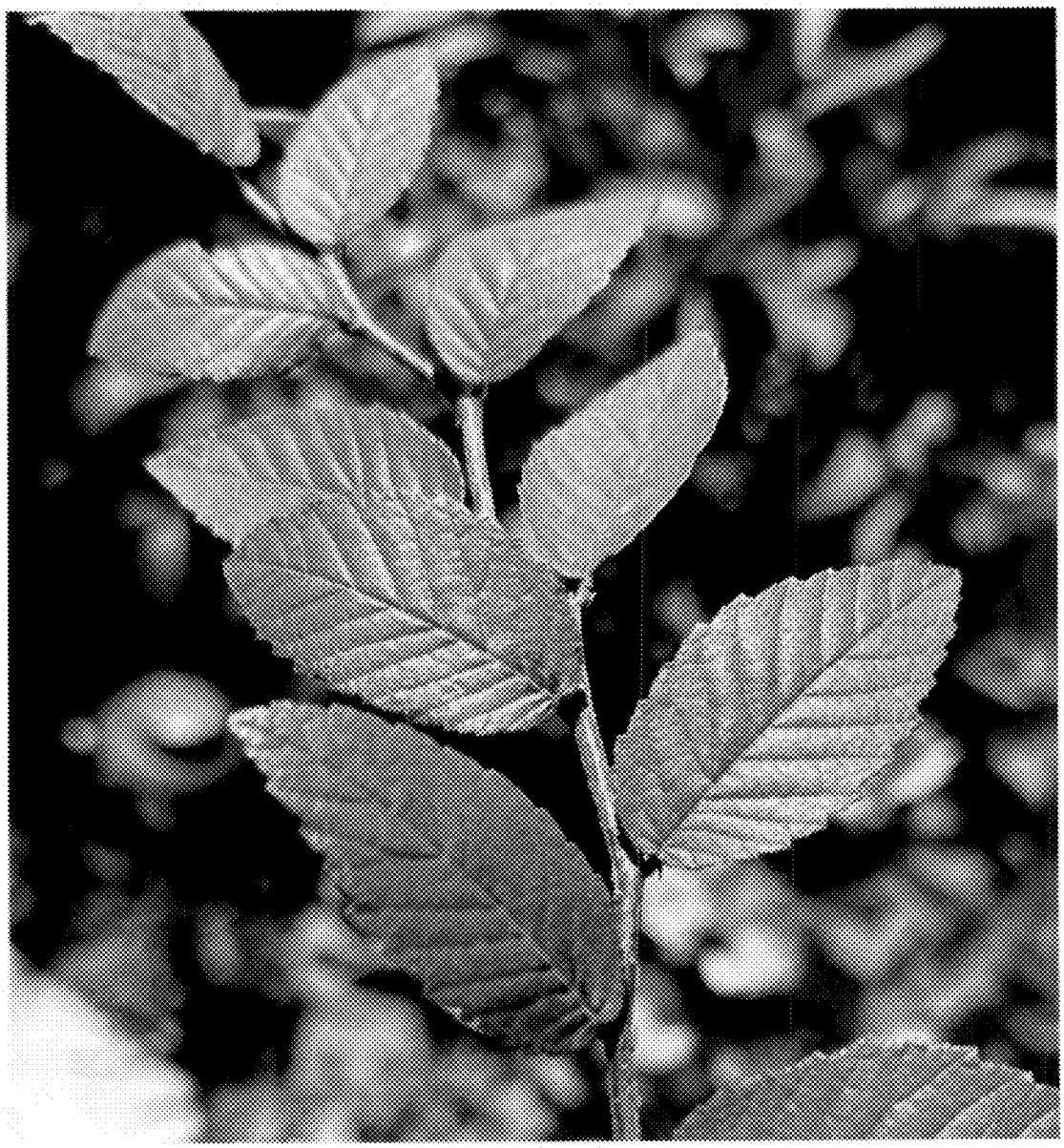

The photograph in FIG. 3 provides a close-up view of the foliage of 'Everalan'.

The colors in the photographs may differ slightly from the color values cited in the detailed botanical description, which accurately describe the colors of the new *Ulmus*.

DETAILED BOTANICAL DESCRIPTION

The following is a detailed description of a 2-year-old tree of 'Everalan' as grown outdoors in a 4-gallon container in Glen Flora, Texas. The phenotype of the new cultivar may vary with variations in environmental, climatic, and cultural conditions, as it has not been tested under all possible environmental conditions. The color determination is in accordance with the 2001 and 2015 Colour Charts of The Royal Horticultural Society, London, England, except where general color terms of ordinary dictionary significance are used.

General description:

*Plant type.*—Deciduous tree.

*Plant habit.*—Upright, tightly narrow.

*Height and spread.*—Average of 2 m in height and 34 cm in width as a 2-year-old tree in a container, reaches about 8 m in height and 2 m in width with a trunk 20 cm in diameter (1 m from soil line) as a 4-year-old tree in the landscape.

*Cold hardiness.*—At least to U.S.D.A. Zones 4c to 7b.

*Diseases and pests.*—No pest problems have been observed, observed and tested to be resistant to Dutch elm disease (caused by *Ascomycota* sp.) and elm beetles.

*Environmental conditions.*—Tolerant to a variety of extreme environmental conditions including wind, ice, snow load, flooding rainfalls and drought.

*Root description.*—Fibrous, fine, freely branched, N167A in color.

*Propagation.*—Root and stem cuttings.

*Root development.*—Average of 25 days to initiate roots, 3 months to produce rooted cutting.

*Growth rate.*—Vigorous, about 1 m per year.

Branch description:

*Branch shape.*—Rounded, wavy.

*Branch color.*—Young; 184A in color, mature; N200A, scaly ridges N167A in color, older wood and bark; 202B.

*Branching.*—Tightly branches, lateral branches held in 45° angles from main, upward facing.

*Branch size.*—Main; an average of 1.3 m in length and 1.5 cm in diameter, lateral; up to 63 cm in length and an average of 3 mm in diameter, and secondary; an average of 21 cm in length and 2 mm in diameter.

*Branch surface.*—Young; smooth, velvety in appearance, and densely covered with soft pubescent hairs 145A in color, 0.4 mm in length, mature; covered in an interlaced pattern of rough and scaly ridges, moderately lenticellate; an average of 10 lenticels per 1 cm, oblong in shape, 1 mm in length, 0.3 mm in width, N167A in color, areas in between are smooth and matte, older wood and trunk; sparsely lenticellate; an average of 6 lenticels per 1 cm; oblong in shape, 0.8 mm in length, 0.4 mm in width, N170A in color, areas in between are smooth and matte.

Foliage description:

*Leaf shape.*—Elliptic to ovate.

*Leaf division.*—Simple.

*Leaf aspect.*—Upward to horizontal.

*Leaf base.*—Oblique.

*Leaf apex.*—Acute.

*Leaf fragrance.*—None.

*Leaf quantity.*—Average of 22 per lateral stem.

*Leaf venation.*—Pinnate, upper surface matches leaf color, main vein slightly distinguishable 145A in color, lower surface veins raised off surface and 193A in color.

*Leaf margins.*—Serrate.

*Leaf arrangement.*—Alternate.

*Leaf internode length.*—An average of 2 cm.

*Leaf attachment.*—Sessile.

*Leaf surface.*—Both surfaces are matte, dry, sticky to the touch due to minute pubescence.

*Leaf size.*—Average of 4.5 cm in length, 2 cm in width.

*Leaf color.*—Young upper and lower surface; 144A, mature upper surface; 137A, mature lower surface; 144A, fall color both surfaces; 164A to 164C.

Flower description:

*Flowers.*—Typical for the species, not present on plants available for data collection.

*Fruit/seed.*—Typical for species, not present on plants available for data collection.

It is claimed:

1. A new and distinct cultivar of *Ulmus* tree named 'Everalan' as herein illustrated and described.

* * * * *